(12) United States Patent
Bertens

(10) Patent No.: US 9,345,443 B2
(45) Date of Patent: May 24, 2016

(54) CALIBRATION FREE DUAL ENERGY RADIOGRAPHY METHOD

(75) Inventor: Tom Bertens, Perk (BE)

(73) Assignee: Agfa HealthCare NV, Mortsel (BE)

( * ) Notice: Subject to any disclaimer, the term of this patent is extended or adjusted under 35 U.S.C. 154(b) by 275 days.

(21) Appl. No.: 14/342,556

(22) PCT Filed: Sep. 4, 2012

(86) PCT No.: PCT/EP2012/067153
§ 371 (c)(1),
(2), (4) Date: Mar. 4, 2014

(87) PCT Pub. No.: WO2013/037659
PCT Pub. Date: Mar. 21, 2013

(65) Prior Publication Data
US 2014/0219423 A1   Aug. 7, 2014

Related U.S. Application Data

(60) Provisional application No. 61/534,026, filed on Sep. 13, 2011.

(30) Foreign Application Priority Data

Sep. 12, 2011   (EP) .................................. 11180932

(51) Int. Cl.
*A61B 6/00*   (2006.01)
*A61B 6/03*   (2006.01)
*G06T 5/50*   (2006.01)

(52) U.S. Cl.
CPC ............... *A61B 6/5241* (2013.01); *A61B 6/032* (2013.01); *A61B 6/482* (2013.01); *A61B 6/505* (2013.01); *A61B 6/5229* (2013.01); *A61B 6/5235* (2013.01); *G06T 5/50* (2013.01);
(Continued)

(58) Field of Classification Search
CPC ........................................................ A61B 6/00
See application file for complete search history.

(56) References Cited

U.S. PATENT DOCUMENTS 5,148,455 A * 9/1992 Stein ...................... A61B 6/405
378/207
6,683,934 B1   1/2004 Zhao et al.
(Continued)

FOREIGN PATENT DOCUMENTS

WO   02/19909 A1   3/2002

OTHER PUBLICATIONS

Kashani et al., "Development of a High-performance Dual-energy Chest Imaging System: Initial Investigation of Diagnostic Performance", Academic Radiology, vol. 16, No. 4, Apr. 2009, pp. 464-476, Reston, VA.
(Continued)

*Primary Examiner* — Robert Kim
*Assistant Examiner* — Eliza Osenbaugh-Stewart
(74) *Attorney, Agent, or Firm* — Keating and Bennett, LLP

(57) ABSTRACT

A method of generating a bone and a soft tissue image of an object includes a dual energy radiography technique wherein weight parameters for calculating these images as a weighted sum of a low energy image $P_L$ and a high energy image $P_H$ are deduced from a ratio image $Log(P_n)/Log(P_L)$.

10 Claims, 5 Drawing Sheets

(52) U.S. Cl.
CPC ............... *G06T2207/10116* (2013.01); *G06T 2207/20224* (2013.01); *G06T 2207/30008* (2013.01)

(56) References Cited

U.S. PATENT DOCUMENTS

2006/0109951 A1    5/2006  Popescu
2009/0207966 A1*   8/2009  Shkumat ............. A61B 6/4035
                                                          378/5

OTHER PUBLICATIONS

Shkumat et al., "Optimization of image acquisition techniques for dual-energy imaging of the chest", Medical Physics, vol. 34, No. 10, Sep. 20, 2007, pp. 3904-3915, Melville, NY.

Official Communication issued in International Patent Application No. PCT/EP2012/067153, mailed on Dec. 11, 2012.

* cited by examiner

CALIBRATION FREE DUAL ENERGY RADIOGRAPHY METHOD

CROSS-REFERENCE TO RELATED APPLICATIONS

This application is a 371 National Stage Application of PCT/EP2012/067153, filed Sep. 4, 2012. This application claims the benefit of U.S. Provisional Application No. 61/534,026, filed Sep. 13, 2011, which is incorporated by reference herein in its entirety. In addition, this application claims the benefit of European Application No. 11180932.3, filed Sep. 12, 2011, which is also incorporated by reference herein in its entirety.

BACKGROUND OF THE INVENTION

1. Field of the Invention

The present invention relates to dual energy radiography and more particularly to an automatic, calibration free method for dual energy material decomposition in digital radiography.

2. Description of the Related Art

Dual energy radiography is a technique that involves taking two radiographic images of an object at different radiation energy. A high energy image and a low energy image are combined to form images which highlight different material compositions in the object. Typically in medical imaging applications, bone or soft-tissue images are reconstructed.

There are different types of algorithms to obtain material decomposition images in dual energy radiography.

A first category of algorithms decomposes the high and low energy images into equivalent thicknesses of basis materials. These methods represent the attenuation coefficient as a weighted sum of non-linear basis functions with the weights representing the basis material thicknesses. This technique requires an extensive calibration procedure whereby the high and low energy pixel values are measured for different kVp pairs using a calibration phantom containing a range of thicknesses for both basis materials, usually aluminum and Lucite.

A second category of algorithms compute the decomposition images as a linear weighted log-subtraction of the low and high energy images.

In this straightforward approach it is assumed that images are generated using mono-energetic spectra and that the imaged object consists of 2 materials, bone and soft tissue. The signal at pixel (x,y) in the low and high energy images is given as follows:

$$P_L \sim \text{Exp}(-\mu_{S,L} z_S - \mu_{B,L} z_B)$$

$$P_H \sim \text{Exp}(-\mu_{S,H} z_S - \mu_{B,H} z_B)$$

With $\mu_{S,L}$ and $\mu_{B,L}$ the attenuation coefficients of soft tissue and bone for the low-energy spectrum, $\mu_{S,H}$ and $\mu_{B,H}$ the attenuation coefficients of soft tissue and bone for the high-energy spectrum and $z_S$ and $z_B$ the thicknesses of soft tissue and bone in the patient for pixel position (x, y).

By computing the subtraction of the log-converted images with a weight parameter w, one can generate material specific images.

$$\text{Log}(P_{OUT}) = \text{Log}(P_H) - w\text{Log}(P_L)$$

$$= -\mu_{S,H} z_S - \mu_{B,H} z_B - w(-\mu_{S,L} z_S - \mu_{B,L} z_B)$$

$$= -(\mu_{S,H} - W\mu_{S,L}) z_S - (\mu_{B,H} - W\mu_{B,L}) z_B$$

If the weight parameter is defined as $w_S = \mu_{S,H}/\mu_{S,L}$ a bone image is generated. In a similar way a soft tissue image is generated if the weight parameter is defined as $w_B = \mu_{B,H}/\mu_{B,L}$.

In prior art the weight parameters are manually selected and adjusted by the observer during image review.

In prior art patent WO 02/19909 A1 the weight parameters are automatically computed in an iterative way using cancellation metrics.

SUMMARY OF THE INVENTION

Preferred embodiments of the present invention provide a method to compute the decomposition images (bone and soft tissue images) by a dual energy radiography technique based on weighted log subtraction of low and high energy images wherein the appropriate weight parameters are calculated automatically in a non-iterative, calibration free way and without any knowledge about the applied exposure settings.

The above-mentioned aspects are realized by a method as set described below. Specific features for preferred embodiments of the invention are also described below.

The decomposition into a soft-tissue image and a bone image is computed based on the weighted log subtraction technique whereby the weights are computed using image content analysis without any knowledge about the exposure settings (kVp, filter material), patient size and material attenuation coefficients.

The decomposition is a non-iterative, two step method. In a first step the bone image is reconstructed whereby the weight parameter is obtained from the histogram of the ratios between the log-converted high and low energy image pixel values. In a second step the bone image is analyzed to localize the bone structures in the image. This information is used to compute the appropriate weight parameter to obtain the soft-tissue image out of the low and high energy images.

A preferred method of the present invention is generally implemented in the form of a computer program product adapted to carry out the method steps when run on a signal processor such as a computer. The computer program product is commonly stored in a computer readable carrier medium such as a DVD. Alternatively the computer program product takes the form of an electric signal and can be communicated to a user through electronic communication.

Further advantages and embodiments of the present invention will become apparent from the following description and drawings.

DETAILED DESCRIPTION OF THE PREFERRED EMBODIMENTS

Figure 1:
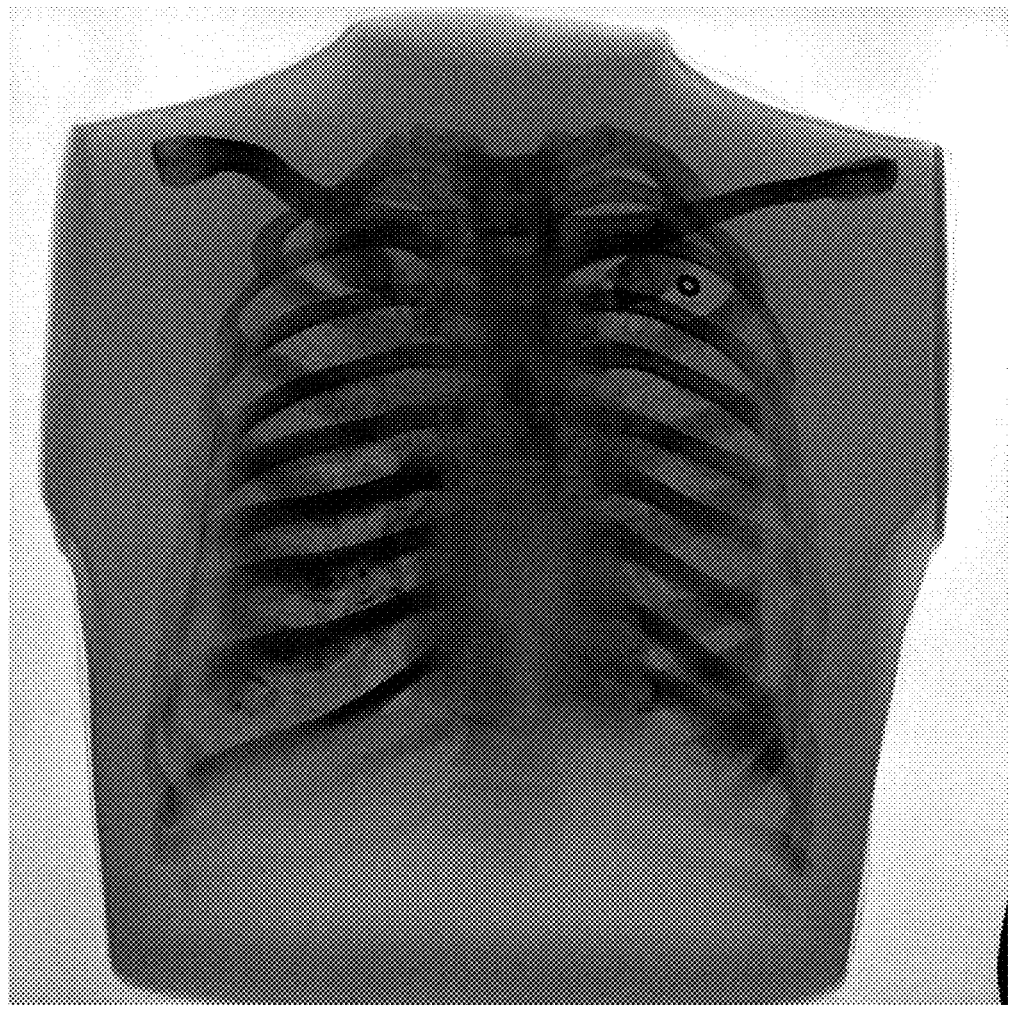
FIG. 1 shows a ratio image of a log converted low energy image and a log converted high energy image.

In dual energy radiography 2 images are generated by an x-ray imaging system, a low energy image and a high energy image.

Such an x-ray system typically comprises an x-ray source and collimator for generating a beam of x-rays which is directed towards the object under examination (a patient, an animal, a test phantom etc.).

The imaging system commonly further comprises a radiation detector for capturing the radiation image of the irradiated object. Examples of suitable radiation detectors are a flat panel solid state radiation detector, a photostimulable phosphor screen, a conventional x-ray film etc.

An image read out device is a part of the imaging system for reading the image stored in the radiation detector and for generating a digital image. This image read out device may be part of the radiation detector itself (e.g. part of the flat panel solid state radiation detector) or may be separate from the detector (e.g. an image digitizer used for detecting light emitted by an exposed photostimulable phosphor screen upon stimulation and for converting into digital pixel values or a film scanner).

The image read out device is further coupled to signal processor in its turn coupled to a memory. The memory stores the digital images read out of the radiation detector and stores a computer program for execution by the signal processor in order to perform the calculations according to preferred embodiments of the present invention which are described below on the digital images.

The signal processor can further be coupled to a display device or to a hard copy recorder for display or hard copy recording of the images that are generated by a method according to a preferred embodiment of the present invention.

The log-subtraction technique allows decomposing the low and high energy images into material specific images, e.g. a bone and soft tissue image in chest radiography:

$$P_{OUT} = \text{Exp}(\text{Log}(P_H) - W\text{Log}(P_L))$$
$$= \text{Exp}(-\mu_{S,H}z_S - \mu_{B,H}z_B - W(-\mu_{S,L}z_S - \mu_{B,L}z_B))$$
$$= \text{Exp}(-(\mu_{S,H} - W\mu_{S,L})z_S - (\mu_{B,H} - W\mu_{B,L})z_B)$$

By choosing the appropriate weight parameters w, a soft tissue image can be reconstructed ($w_B=\mu_{B,H}/\mu_{B,L}$) and a bone image can be reconstructed ($w_S=\mu_{S,H}/\mu_{S,L}$).

A preferred embodiment of the present invention provides a method to compute the appropriate weight parameters automatically in a non-iterative, calibration free way and without any knowledge about the exposure settings.

In case of a dual-exposure system, the low and high energy images are preferably first spatially registered to reduce misalignment artifacts due to cardiac, respiratory, bowel and patient motion. Different rigid and non-rigid registration algorithms are known. (Spatial registration methods are e.g. described extensively in co-pending European patent applications 10169607.8 and 11151202.6).

Additional preprocessing operations can be applied to the registered low and high energy image to reduce the noise, remove the anti-scatter grid line-artifacts, etc.

An appropriate weight parameter to reconstruct the bone image can be computed out of the ratio of the pixel values of pixels of the log converted high energy image and pixel values in corresponding pixel locations in the log converted low energy image:

$$\text{Log}(P_H)/\text{Log}(P_L)=(-\mu_{S,H}z_S-\mu_{B,H}z_B)/(-\mu_{S,L}z_S-\mu_{B,L}z_B)$$

An image which for each pixel comprises a value resulting from the above operation performed on corresponding pixels in the log converted low and high energy images is further on called 'ratio image'.

Figure 2:
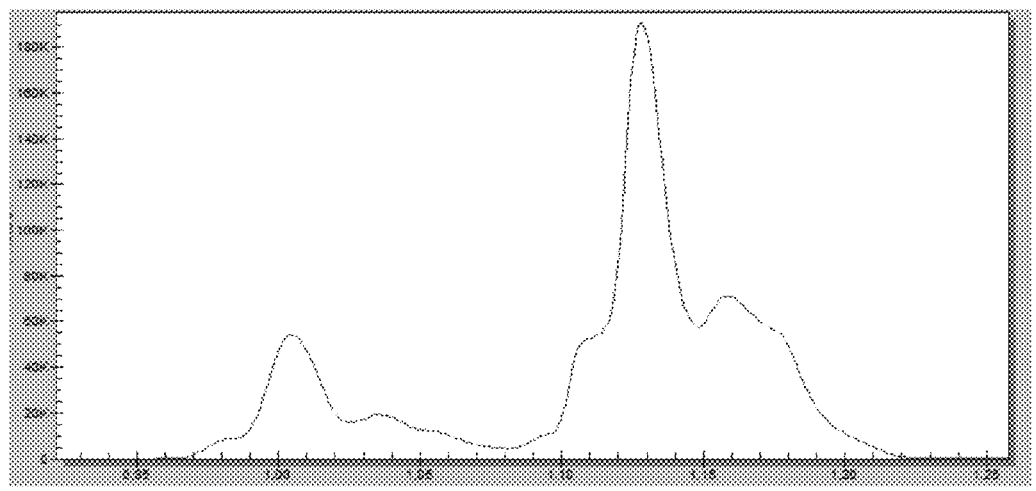
FIG. 2 shows the histogram of the pixel values of the ratio image of FIG. 1.

Mainly 3 regions can be identified in the ratio image (see FIG. 1). A first group of ratios (pixel values of the ratio image) correspond with the direct exposed area. A second group of ratios correspond with pixels originating from only soft tissue attenuation. The last group of ratios correspond with pixels originating from a combination of soft tissue and bone attenuation. This is also reflected in the histogram of the ratio values (see FIG. 2).

For the pixels originating from only soft tissue attenuation, the bone thickness $z_B$ is 0, thus the ratio of log converted pixel values is:

$$\text{Log}(P_H)/\text{Log}(P_L)=-\mu_{S,H}z_S/-\mu_{S,L}z_S=\mu_{S,H}/\mu_{S,L}$$

This is exactly the unknown weight parameter $w_S$ that is needed to reconstruct the bone image.

The weight parameter $w_S$ is computed as the centre of the bin with the maximum counts. As we are interested in the group of ratios corresponding with only soft tissue attenuation, the histogram computation can be made more selective by computing a mask of pixels of interest in the image ignoring the background regions and the bright, mostly bone structures in the image. A good approximation of a mask of pixels of interest can be obtained by thresholding.

Another embodiment is to spatially vary the weight parameter $w_S$ instead of using 1 global weight parameter in the log subtraction. The soft tissue attenuation ratio can vary slightly over the image due to heel effect, tissue thickness variation and scatter.

By dividing the ratio image in regions or tiles and computing the weight parameter $w_S$ per region or tile (in the way described higher), for every pixel in the image the locally most optimal weight parameter $w_S$ can be computed by interpolation.

Figure 3:
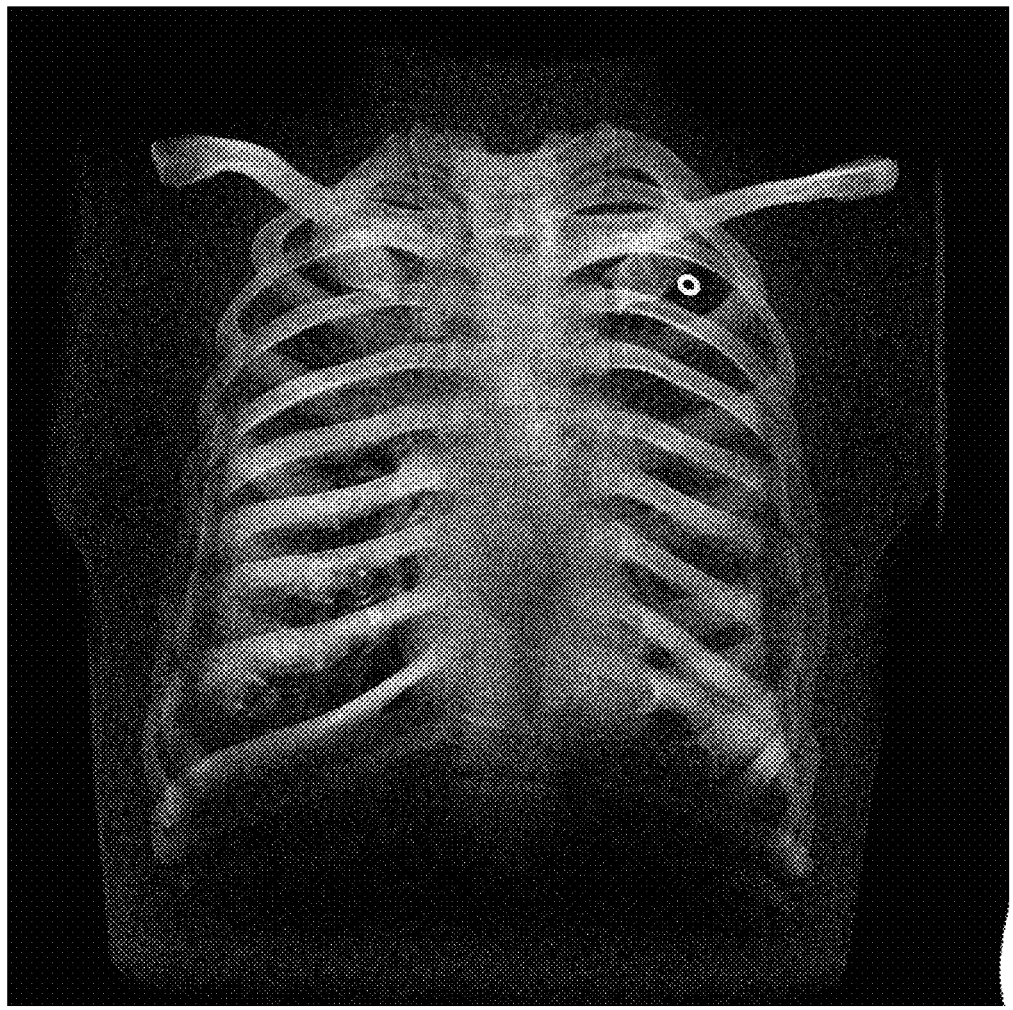
FIG. 3 shows a reconstructed bone image.

The result of the calculation of $P_{bone}=\text{Exp}(\text{Log}(P_H)-w_S\text{Log}(P_L))$ is a reconstructed bone image as shown in FIG. 3.

To reconstruct the soft tissue image, the weight parameter $w_B$ has to be computed which represents the ratio of the attenuation coefficients of bone.

The weight parameter $w_B$ for soft tissue image reconstruction can be computed using the information in the reconstructed bone image.

The bone edges in the reconstructed bone image correspond with image regions where the average local gradient across the bone edge should be zero in the reconstructed soft tissue image.

Figure 4:
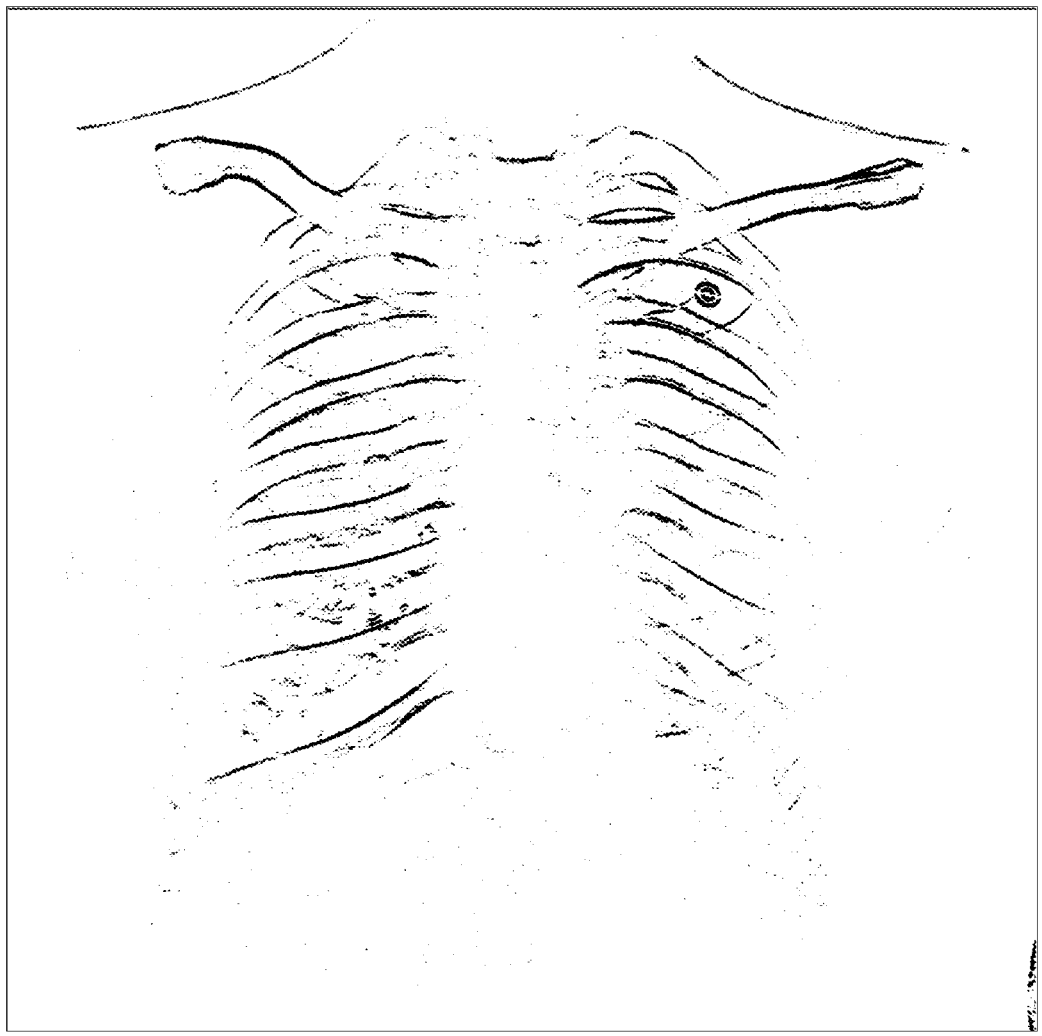
FIG. 4 shows the edges identified in the reconstructed bone image.

The bone edges can e.g. be localized by applying an edge filter to the reconstructed bone image e.g. the Sobel filter (see FIG. 4). Alternative methods to localise the edges are also applicable such as model fitting.

To preserve only a subset of relevant edge pixels, a selective range can be defined for the edge strengths. Edge pixels with a low edge strength can be ignored as irrelevant noisy edges. Edge pixels with a high value of the edge strength can be ignored as they might be edges from implants or misalignment artefacts.

For every bone edge pixel it is required that there is no pixel difference across the bone edge position in the reconstructed soft tissue image.

For every bone edge pixel 2 pixel positions are computed adjacent to the bone edge and situated on opposite sides of an edge, e.g. pixel values pairs are computed in opposite pixel positions perpendicular to the bone edge direction. As the pixel values of these 2 pixels should be equal in the reconstructed bone image:

$$\text{Log}(P_{H,1})-w_B\text{Log}(P_{L,1})=\text{Log}(P_{H,2})-w_B\text{Log}(P_{L,2})$$

Or $$w_B\text{Log}(P_{L,1})-w_B\text{Log}(P_{L,2})=\text{Log}(P_{H,1})-\text{Log}(P_{H,2})$$

Or $$w_B=(\text{Log}(P_{H,1})-\text{Log}(P_{H,2}))/\text{Log}(P_{L,1})-\text{Log}(P_{L,2}))$$

The weight parameter $w_B$ is computed as the median of the ratios of the pixel differences over the bone edge pixels in the log-converted high energy image and the pixel differences in the log-converted low energy image.

Alternative values can be envisaged such as the average value or a predefined percentile etc.

In another embodiment the weight parameter $w_B$ can be spatially varied in a similar way as the computation of $w_S$. This allows taking into account slight variations of the weight parameter $w_B$ due to the heel effect, bone thickness variation and scatter. The bone edge mask can be divided in regions or tiles and the weight parameter $w_B$ is then computed per region or tile. For every pixel in the image the locally most optimal weight parameter $w_B$ can be computed by interpolation.

Figure 5:
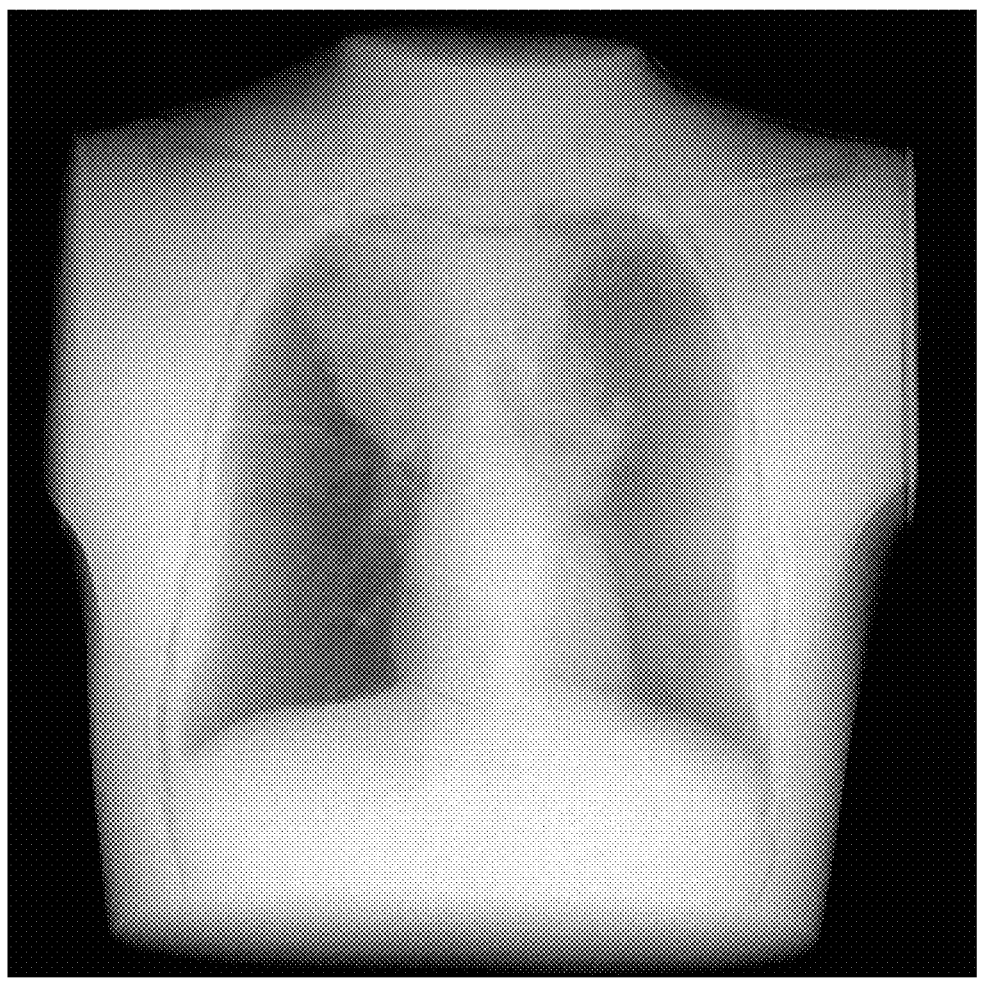
FIG. 5 shows the reconstructed soft tissue image.

The result of the calculation of $P_{soft}=\text{Exp}(\text{Log}(P_H)-w_B\text{Log}(P_L))$ is a reconstructed soft tissue image as shown in FIG. 5.

Post-processing operations can be applied to the reconstructed bone and soft tissue images to reduce noise, to apply scatter corrections and to convert the pixel values to values suitable for reproduction or displaying, e.g. using known multiscale image processing methods as there are multiscale gradation processing (as described in EP 1 341 125) and multiscale contrast enhancement processing (as described in EP 1 347 413).

While preferred embodiments of the present invention have been described above, it is to be understood that variations and modifications will be apparent to those skilled in the art without departing from the scope and spirit of the present invention. The scope of the present invention, therefore, is to be determined solely by the following claims.

The invention claimed is:

1. A method for generating a bone and a soft tissue image of an object by a dual energy radiography technique wherein the bone and the soft tissue images are calculated as weighted log-subtractions of low energy and high energy images, the method comprising the steps of:
   generating a high energy radiation image $P_H$ of the object with a first energy level with a source of radiation;
   generating a low energy radiation image $P_L$ of the object with a second energy level with a source of radiation lower than the first energy level;
   calculating a ratio image $\text{Log}(P_H)/\text{Log}(P_L)$;
   computing at least one value of a weight parameter $w_S$ by using pixel values of the ratio image;
   generating a bone image as $P_{bone}=\text{Exp}(\text{Log}(P_H)-w_S\text{Log}(P_L))$;
   localizing bone edges in the bone image;
   computing at least one value of a weight parameter $w_B$ from pixel values of pixel pairs of pixels adjacent to at least one of the bone edges and situated on opposite sides of the at least one of the bone edges; and
   reconstructing a soft tissue image as $P_{soft}=\text{Exp}(\text{Log}(P_H)-w_B\text{Log}(P_L))$.

2. The method according to claim 1, wherein the weight parameter $w_S$ is determined by the steps of:
   calculating a histogram of the pixel values of the ratio image; and
   computing $w_S$ as a center of a bin with maximum counts in the histogram.

3. The method according to claim 2, wherein a mask of pixels of interest is computed, the mask includes pixels of the ratio image with exception of pixels of background regions and bright structures, and only masked pixels are taken into account when calculating the histogram.

4. The method according to claim 1, wherein the bone edges are localized by subjecting the bone image to an edge filtering operation.

5. The method according to claim 1, wherein the weight parameter $w_B$ is calculated as an average value, a median value, or a preset percentile of ratios of differences of the pixel values of the pairs of pixels in the log converted high energy image $\text{Log}(P_H)$ and in the log converted low energy image $\text{Log}(P_L)$.

6. The method according to claim 1, wherein the low and high energy images are spatially registered prior to the step of calculating the ratio image.

7. The method according to claim 1, wherein the low and high energy images are pre-processed prior to the step of calculating the ratio image.

8. The method according to claim 1, wherein the ratio image is divided into tiles, the weight parameter $w_S$ and/or the weight parameter $w_B$ is calculated for each of the tiles, and for each pixel an optimal weight parameter is computed by interpolation between the calculated values of the weight parameters $w_S$ and $w_B$.

9. A non-transitory computer readable medium comprising computer executable program code for carrying out, when the computer program is executed on a computer, the steps of claim 1.

10. A non-transitory computer readable medium including a computer program including computer code for carrying out, when the computer program is executed on a computer, a method of obtaining a high energy radiation image $P_H$ of an object by radiation of the object with a first energy level with a source of radiation and a low energy radiation image $P_L$ of the object by irradiating the object with a second energy level with a source of radiation lower than the first energy level, the method comprising the steps of:
   calculating a ratio image $\text{Log}(P_H)/\text{Log}(P_L)$;
   computing at least one value of a weight parameter $w_S$ by using pixel values of the ratio image;
   generating a bone image as $P_{bone}=\text{Exp}(\text{Log}(P_H)-w_S\text{Log}(P_L))$;
   localizing bone edges in the bone image;
   computing at least one value of a weight parameter $w_B$ from pixel values of pixel pairs of pixels adjacent to at least one of the bone edges and situated on opposite sides of the at least one of the bone edges; and
   reconstructing a soft tissue image as $P_{soft}=\text{Exp}(\text{Log}(P_H)-w_B\text{Log}(P_L))$.

\* \* \* \* \*